(12) United States Patent
Berme et al.

(10) Patent No.: US 10,736,545 B1
(45) Date of Patent: Aug. 11, 2020

(54) PORTABLE SYSTEM FOR VESTIBULAR TESTING AND/OR TRAINING OF A USER

(71) Applicant: Bertec Corporation, Columbus, OH (US)

(72) Inventors: Necip Berme, Worthington, OH (US); Cameron Scott Hobson, London, OH (US); Qian Wang, Westfield, IN (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 16/439,291

(22) Filed: Jun. 12, 2019

Related U.S. Application Data

(60) Provisional application No. 62/688,334, filed on Jun. 21, 2018.

(51) Int. Cl.
*A61B 5/00* (2006.01)
*A61B 5/12* (2006.01)
(Continued)

(52) U.S. Cl.
CPC ............ *A61B 5/123* (2013.01); *A61B 5/0022* (2013.01); *A61B 5/742* (2013.01);
(Continued)

(58) Field of Classification Search
CPC ....... A61B 5/123; A61B 5/0022; A61B 5/742; A61B 2562/0219; A63B 24/0062;
(Continued)

(56) References Cited

U.S. PATENT DOCUMENTS 6,038,488 A   3/2000  Barnes et al.
6,113,237 A   9/2000  Ober et al.
(Continued)

FOREIGN PATENT DOCUMENTS

WO   2017/127606 A1   7/2017

OTHER PUBLICATIONS

Eye Tracker with Scene Camera, SR Research Website, Web page <http://www.sr-research.com/EL_II_scam.html>, 1 page, dated Apr. 22, 2012, retrieved from Internet Archive Wayback Machine <https://web.archive.org/web/20120422195146/http://www.sr-research.com/EL_II_scam.html> on Oct. 15, 2014.

(Continued)

*Primary Examiner* — George Manuel
(74) *Attorney, Agent, or Firm* — The Law Office of Patrick F. O'Reilly III, LLC

(57) ABSTRACT

A portable system for vestibular testing and/or training of a user is disclosed herein. The system includes a user input device, the user input device configured to output a signal based upon an input response by the user; a motion sensing device, the motion sensing device configured to measure a velocity or speed of a head of the user; a visual display device, the visual display device configured to display one or more visual objects so that the one or more visual objects are visible to the user; and a data processing device operatively coupled to the user input device, the motion sensing device, and the visual display device. The data processing device is programmed to determine whether or not the user correctly identifies the one or more visual objects displayed on the visual display device based upon the signal from the user input device.

21 Claims, 4 Drawing Sheets

(51) Int. Cl.
    *A63B 24/00* (2006.01)
    *G06F 3/01* (2006.01)
(52) U.S. Cl.
    CPC ...... *A63B 24/0062* (2013.01); *A63B 24/0087* (2013.01); *G06F 3/012* (2013.01); *G06F 3/013* (2013.01); *G06F 3/017* (2013.01); *A61B 2562/0219* (2013.01); *A63B 2024/0093* (2013.01)
(58) Field of Classification Search
    CPC ........ A63B 24/0087; A63B 2024/0093; G06F 3/012; G06F 3/013; G06F 3/017
    See application file for complete search history.

(56) References Cited

U.S. PATENT DOCUMENTS

| | | | |
|---|---|---|---|
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,936,016 B2 | 8/2005 | Berme et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 | 4/2014 | Berme et al. | |
| 8,764,532 B1 | 7/2014 | Berme | |
| 8,847,989 B1 | 9/2014 | Berme et al. | |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 9,916,011 B1 | 3/2018 | Berme et al. | |
| 9,927,312 B1 | 3/2018 | Berme et al. | |
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 2003/0216656 A1 | 11/2003 | Berme et al. | |
| 2008/0228110 A1 | 9/2008 | Berme | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2015/0096387 A1 | 4/2015 | Berme et al. | |
| 2016/0242642 A1* | 8/2016 | Migliaccio | A61B 3/113 |
| 2016/0245711 A1 | 8/2016 | Berme et al. | |
| 2016/0334288 A1 | 11/2016 | Berme et al. | |
| 2017/0365101 A1* | 12/2017 | Samec | G02B 27/017 |
| 2018/0024015 A1 | 1/2018 | Berme et al. | |
| 2019/0078951 A1 | 3/2019 | Berme et al. | |

OTHER PUBLICATIONS

Eye Gaze Tracking Under Natural Head Movements, Zhiwei Zhu and Qiang Ji, 2005 IEEE.
Efficient real-time algorithms for eye state and head pose tracking in Advanced Driver Support Systems, Riad L. Hammoud, Andrew Wilhelm, Phillip Malawey, and Gerald J. Witt, 2005, IEEE.
Combined Head and Eye Tracking System for Dynamic Testing of the Vestibular System, Robert S. Allison, Moshe Eizenman, and Bob S. K. Cheung, IEEE Transactions on Biomedical Engineering, vol. 41, No. 11, Nov. 1996.
Active Eye-Tracking System by Using Quad PTZ Cameras, Chao-Ning Chan, Shunichiro Oe, Chem-Sheng Lint, IEEE 2007.
A Cascaded Scheme for Eye Tracking and Head Movement Compensation, X. Xie, R. Sudhakar, H. Zhuang, Systems and Humans, vol. 28, No. 4, Jul. 1998.

* cited by examiner

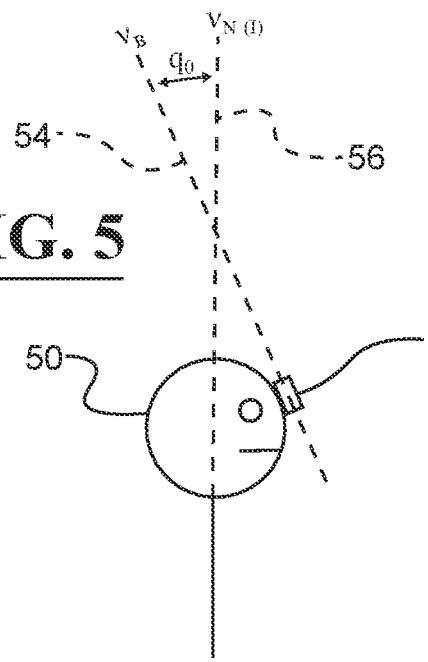
FIG. 5
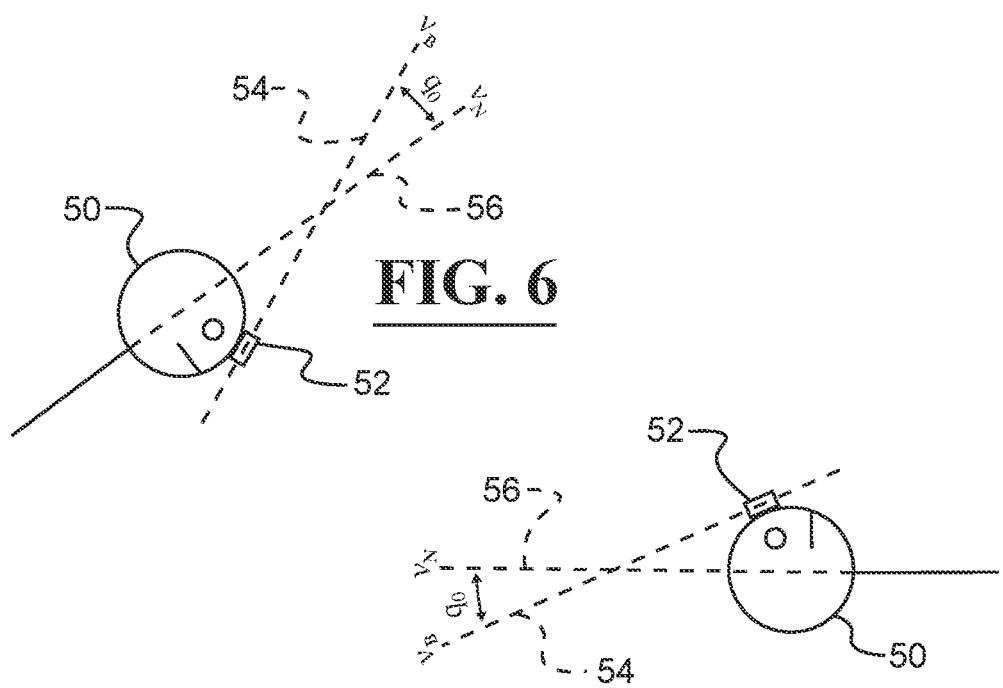
FIG. 6
FIG. 7

PORTABLE SYSTEM FOR VESTIBULAR TESTING AND/OR TRAINING OF A USER

CROSS-REFERENCE TO RELATED APPLICATIONS

This patent application claims priority to, and incorporates by reference in its entirety, U.S. Provisional Patent Application No. 62/688,334, entitled "Portable System For Vestibular Testing And/Or Training Of A User", filed on Jun. 21, 2018.

BACKGROUND OF THE INVENTION

1. Field of the Invention

The invention generally relates to a portable system for vestibular testing and/or training of a user. More particularly, the invention relates to a portable system for vestibular testing and/or training of a user that enables a user to perform vestibular testing and/or training exercises in a myriad of different locations without the onsite presence of a clinician or therapist being necessary.

2. Background

Many individuals experience concussions in the course of their lives. For example, athletes often sustain concussions while playing a particular sport, such as football or soccer. Frequently, one of the main consequences of a concussion is the impairment of vestibular function. Impairments in vestibular function are known to adversely affect dynamic visual acuity, and to cause blurred vision and poor visual focus when the concussed individual displaces his or her head. Gaze stabilization exercises have been demonstrated to improve impairments in individuals with vestibular dysfunction, but to realize such an improvement, the concussed individual must perform the exercises on a regular and frequent basis (e.g., multiple times per day). However, because these exercises are typically required to be performed using equipment that is only available in the office of a clinician or therapist, it is very difficult for a concussed individual to perform these exercises on the regular basis that is needed for improvement in vestibular function. Also, the conventional exercises performed are not sufficiently engaging for the concussed individual, which often results in the individual losing interest in the exercises and/or underperforming during the execution of the exercises.

What is needed, therefore, is a portable system for vestibular testing and/or training of a user that enables testing and/or training sessions to be performed in many different locations, such as in the home of the user, or on the sidelines at a sporting event. Moreover, a portable system for vestibular testing and/or training of a user is needed that sufficiently engages the user in a training session so that the user is able to realize a substantial benefit from the training. Furthermore, a need exists for a portable system for vestibular testing and/or training of a user that is capable of communicating with a remote electronic device so that a remote user, such as a clinician or therapist, is able to monitor the testing and/or training being performed by the user.

BRIEF SUMMARY OF EMBODIMENTS OF THE INVENTION

Accordingly, the present invention is directed to a portable system for vestibular testing and/or training of a user that substantially obviates one or more problems resulting from the limitations and deficiencies of the related art.

In accordance with one or more embodiments of the present invention, there is provided a portable system for vestibular testing and/or training of a user. The system includes a user input device, the user input device configured to output a signal based upon an input response by the user; a motion sensing device, the motion sensing device configured to measure a velocity or speed of a head of the user; a visual display device having an output screen, the visual display device configured to display one or more visual objects on the output screen so that the one or more visual objects are visible to the user; and a data processing device, the data processing device operatively coupled to the user input device, the motion sensing device, and the visual display device. The data processing device being programmed to display one or more visual objects on the output screen of the visual display device while the user's head undergoes displacement at a velocity or speed within a predetermined range as measured by the motion sensing device, the one or more visual objects being superimposed on a dynamic background displayed on the output screen of the visual display device; and the data processing device being further programmed to determine whether or not the user correctly identifies the one or more visual objects based upon the signal from the user input device.

In a further embodiment of the present invention, the motion sensing device comprises an inertial measurement unit that includes at least one of an accelerometer, a gyroscope, and a magnetometer; and the data processing device is operatively coupled to the inertial measurement unit by means of a wireless connection.

In yet a further embodiment, the user input device comprises at least one of: (i) a touchscreen user interface, (ii) a voice recognition device, (iii) one or more buttons, (iv) a keyboard, (v) a clicking device, and (vi) a joystick; and the user input device is configured to accept a plurality of different responses from the user, each of the plurality of different responses of the user corresponding to a different visual object.

In still a further embodiment, the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

In yet a further embodiment, the user input device, the visual display device, and the data processing device are constituent components of a handheld tablet computing device or a laptop computing device.

In still a further embodiment, the portable system further comprises a camera configured to capture a plurality of eye images of the user while the user is being tested using the system; and the data processing device is further operatively coupled to the camera, the data processing device being configured to determine the eye movement of the user based upon the plurality of eye images of the user captured by the camera.

In yet a further embodiment, the portable system further comprises an eye movement tracking device configured to track eye movement and/or eye position of the user, the eye movement tracking device comprising at least one of the following: (i) a video camera, (ii) an infrared sensor, (iii) an ultrasonic sensor, and (iv) an electrooculographic sensor. The data processing device is further operatively coupled to the video camera, the infrared sensor, the ultrasonic sensor, and/or the electrooculographic sensor, the data processing device being configured to determine the eye movement and/or eye position of the user based upon output from the video camera, the infrared sensor, the ultrasonic sensor, and/or the electrooculographic sensor.

In still a further embodiment, the portable system further comprises means for determining a distance and/or tilt of the head of the user relative to the visual display device; and the means for determining a distance and/or tilt of the head of the user comprises a camera configured to capture one or more images of a visual feature on the head of the user, or a distance detection device with a transmitter portion for emitting an ultrasonic or infrared pulse and a receiver portion for receiving the ultrasonic or infrared pulse after it is reflected off the head of the user.

In yet a further embodiment, the means for determining a distance and/or tilt of the head of the user comprises a camera configured to capture one or more images of a visual feature on the head of the user; and the data processing device is further operatively coupled to the camera, the data processing device being configured to determine the distance between the head of the user and the visual display device based upon a size of the visual feature in the one or more images captured by the camera, and the data processing device is further configured to determine the tilt of the head of the user relative to the visual display device based upon a size comparison of two or more adjacent visual features in the one or more images captured by the camera, or based upon a distortion of the visual feature in the one or more images captured by the camera.

In still a further embodiment, the portable system further comprises a data interface operatively coupling the data processing device of the portable system to a remote electronic device via a network so that data from the data processing device is capable of being transmitted to the remote electronic device; and the data interface comprises a wireless data interface or a wired data interface operatively coupled to the data processing device, and the network coupling the data processing device of the portable system to the remote electronic device comprises an internet-based network.

In yet a further embodiment, the data processing device is further programmed to generate one or more interactive exercises for the user containing the one or more visual objects on the output screen of the visual display device, the one or more interactive exercises including one or more parameters affecting the difficulty of the one or more interactive exercises for the user; and the remote electronic device is programmed so as to allow a remote user to modify the one or more parameters affecting the difficulty of the one or more interactive exercises for the user.

In still a further embodiment, the dynamic background on which the one or more visual objects are superimposed comprises one or more scenes of a movie; and the one or more parameters affecting the difficulty of the one or more interactive exercises for the user comprise a location of the one or more visual objects on the output screen of the visual display device.

In yet a further embodiment, the one or more interactive exercises generated by the data processing device comprise a plurality of different levels. The data processing device is further programmed to advance to a successive one of the plurality of different levels when the user performs a particular one of the one or more interactive exercises correctly so as to increase the difficulty of the one or more interactive exercises. The data processing device is further programmed to adjust the location of the one or more visual objects on the output screen of the visual display device from a central location on the output screen to a peripheral location on the output screen as the difficulty of the one or more interactive exercises is increased. The remote electronic device is further programmed so as to allow the remote user to advance the user to the successive one of the plurality of different levels via the network.

In still a further embodiment, the remote electronic device is further programmed to generate one or more reports indicative of the performance of the user during the one or more interactive exercises so that the remote user is able to remotely track the progress of the user during the one or more interactive exercises and modify the one or more parameters if deemed necessary.

In yet a further embodiment, the portable system further comprises a camera configured to capture one or more images of the user while the user is being tested using the system; and the data processing device is further operatively coupled to the camera, the data processing device being configured to transmit the one or more images of the user captured by the camera to the remote electronic device so that the remote user is able to remotely direct the user on the proper technique for performing the one or more interactive exercises.

In still a further embodiment, the data processing device is further programmed to generate a plurality of different dynamic backgrounds of varying complexity, and to display a particular one of the plurality of different dynamic backgrounds on the output screen of the visual display device together with the one or more visual objects, and the data processing device is further programmed to select the particular one of the plurality of different visual backgrounds that is displayed on the output screen of the visual display device based upon a difficulty level of a visual exercise being performed by the user.

In yet a further embodiment, the data processing device is further programmed to generate a game-type user interface with the one or more visual objects disposed on the particular one of the plurality of different dynamic backgrounds and a score indicating a quantity of the one or more visual objects identified correctly by the user; and the game-type user interface generated by the data processing device further includes a game performance summary indicating a total quantity of the one or more visual objects that the user has attempted to identify, and the difficulty level of the visual exercise, in the addition to the score.

In still a further embodiment, the dynamic background on which the one or more visual objects are superimposed comprises one or more scenes of a movie; and the data processing device is further programmed to determine which ones of the one or more visual objects are displayed on the output screen of the visual display device based upon a particular theme selected by the user using the user input device.

In yet a further embodiment, the data processing device is programmed to determine an angular velocity of the head of the user about an inertial frame neck axis of the user using output data from the motion sensing device so that the angular velocity of the head of the user is capable of being accurately determined regardless of the orientation of the user.

In still a further embodiment, the data processing device is further programmed to determine the angular velocity of the head of the user about the inertial frame neck axis of the user by using quaternion angles to transform the angular velocity of the head of the user about a body frame axis determined using output data from the motion sensing device to the angular velocity of the head of the user about the inertial frame neck axis of the user.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 5 is a diagrammatic view of an inertial measurement unit disposed on the head of a user, wherein the head of the user is disposed in an upright position;

FIG. 6 is another diagrammatic view of an inertial measurement unit disposed on the head of a user, wherein the head of the user is in a forward leaning position; and FIG. 7 is yet another diagrammatic view of an inertial measurement unit disposed on the head of a user, wherein the head of the user is in a supine position.

Throughout the figures, the same parts are always denoted using the same reference characters so that, as a general rule, they will only be described once.

DETAILED DESCRIPTION OF EMBODIMENTS OF THE INVENTION

The present invention is described herein, in an exemplary manner, with reference to computer system architecture and exemplary processes carried out by the computer system. In one or more embodiments, the functionality described herein can be implemented by computer system instructions. These computer program instructions may be loaded directly onto an internal data storage device of a computing device (e.g., an internal data storage device of a tablet computing device). Alternatively, these computer program instructions could be stored on a portable computer-readable medium (e.g., a flash drive, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software.

This description describes in general form the computer program(s) required to carry out the vestibular testing and/or training of a user. Any competent programmer in the field of information technology could develop a system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. In addition to that which is explicitly depicted, it is to be understood that many alternative or additional functional relationships and/or physical connections may be incorporated in a practical application of the system.

1. Illustrative Vestibular Testing and/or Training System

Figure 1:
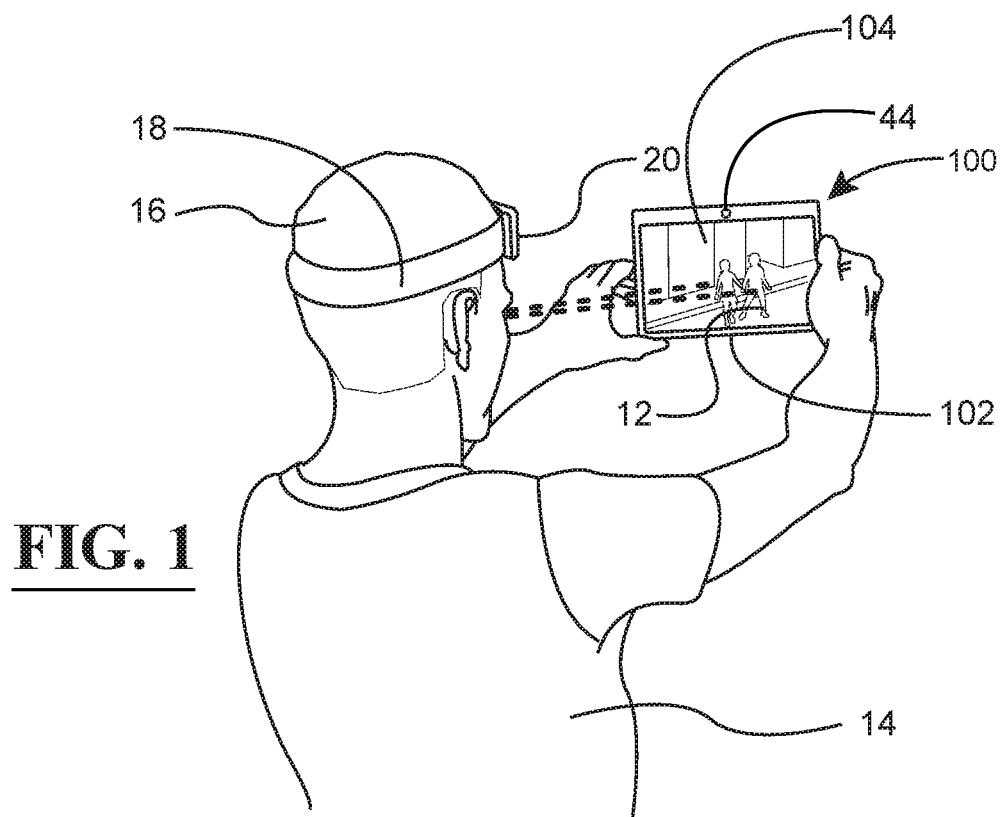
FIG. 1 is a diagrammatic perspective view of a portable vestibular testing and/or training system, according to one embodiment of the invention, wherein the user is watching a movie on a tablet computing device, and the user is not yet moving his head.
Figure 2:
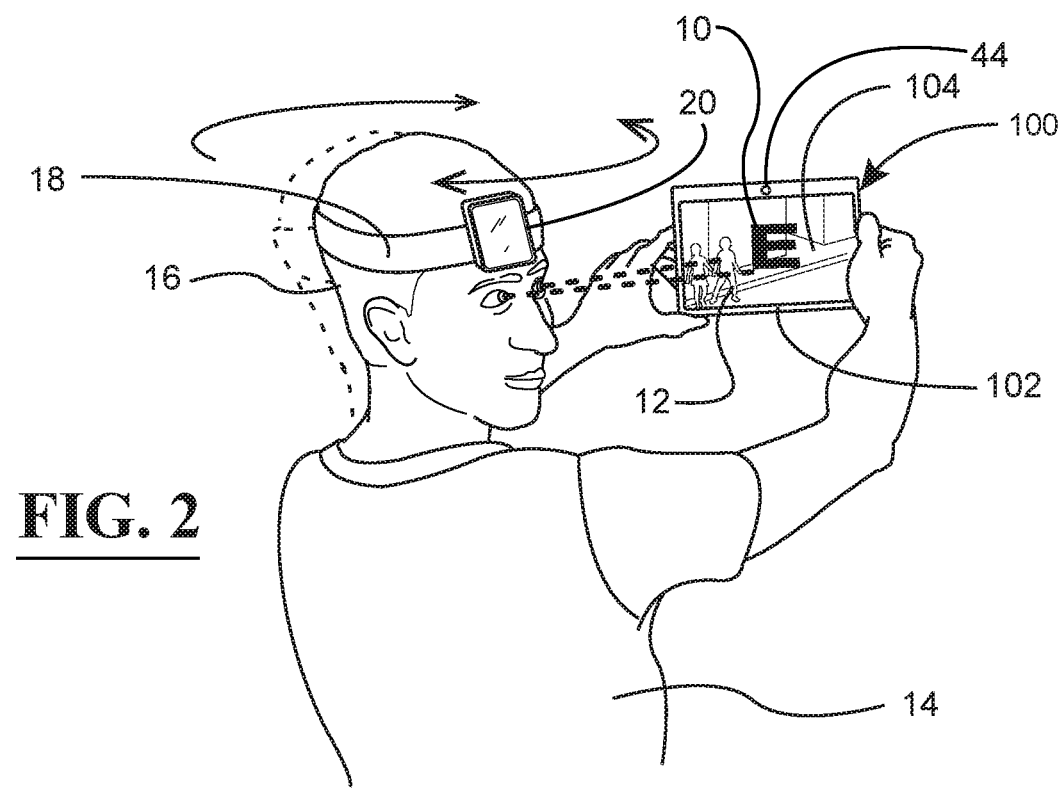
FIG. 2 is another diagrammatic perspective view of a portable vestibular testing and/or training system, wherein an optotype is superimposed on a scene of the movie while the user is displacing his head back-and-forth within a prescribed range.

A first illustrative embodiment of a portable system for vestibular testing and/or training of a user is seen generally at 100 in FIGS. 1 and 2. In the illustrative embodiment, the portable vestibular testing and/or training system 100 generally comprises a tablet computing device 102 with a visual display device 104. The tablet computing device 102 is one illustrative form of a data processing device and/or data processing and data acquisition device. In FIGS. 1 and 2, the tablet computing device 102 is being held by the user 14 while the user is standing. In one or more embodiments, the center of the visual display device 104 of the tablet computing device 102, which contains the one or more identifiable visual objects 10, is generally aligned with the eyes of the user 14 (i.e., so the user 14 is looking straight at the visual object 10 on the visual display device 104 during the testing and/or training).

The one or more visual objects 10 (e.g., identifiable visual objects 10 superimposed on a movie scene 12), which the user identifies during each vestibular test and/or training session described herein, are displayed on the visual display device 104 of the tablet computing device 102 in the illustrative embodiment. Specifically, as shown in FIG. 2, the visual object 10 is displayed on the output screen of the tablet visual display device 104 in the approximate center of the screen.

In addition, while the visual object 10 in FIG. 2 is in the form of an optotype (e.g., a Tumbling E), it is to be understood that other suitable visual objects 10 may be used in place of the Tumbling E optotype. For example, the visual object 10 alternatively may comprise a Landolt C optotype or an optotype comprising different letters of a recognized alphabet (e.g., different letters of the English alphabet). That is, in some embodiments, the user 14 may identify different letters of a recognized alphabet, rather than different orientations of the same letter or optotype. Also, in other embodiments, the visual object 10 alternatively may comprise any other identifiable symbol (e.g., a crescent, a star, etc.).

In one or more embodiments, different letters or objects may be displayed in succession during a particular test or training session. For example, during a particular test or training session, a Tumbling E optotype may be displayed first, then followed by the letter "K", a crescent symbol, a star symbol, etc. In this exemplary fashion, the letters that are displayed to the user 14 can be consistently varied during the performance of the testing or training session.

Referring again to FIGS. 1 and 2, it can be seen that the head 16 of the user 14 is fitted with a motion sensing device 20 disposed thereon. In particular, in the illustrative embodiment, the motion sensing device 20 is removably coupled to the head of the user 14 using a stretchable, elastic headband 18 (i.e., a resilient adjustable band 18). The motion sensing device 20 is configured to measure a velocity or speed and the angular displacement of the head 16 of the user 14 when the head 16 of the user 14 is displaced during the particular test or training session. That is, the motion sensing device 20 determines the angular displacement and velocity of the user's head 16 during the performance of a particular test or training session (e.g., the angular velocity of the user's head 16 in degrees per second). In one or more embodiments, the motion sensing device 20 comprises at least one of an accelerometer and a gyroscope.

In the illustrative embodiment, the motion sensing device 20 may comprise a three-dimensional motion sensing device (i.e., an inertial measurement unit (IMU)) having a 3-axis accelerometer, a 3-axis rate gyro, and a 3-axis compass (i.e., a 3-axis magnetometer). Also, the illustrative motion sensing device 20 may comprise a wireless data connection to the tablet computing device 102. In particular, the tablet computing device 102 may comprise a data transmission interface unit that is operatively connected to one of the output ports of the tablet computing device 102, such as the universal serial bus (USB) port of the tablet computing device 102. As such, the tablet computing device 102 provided with the data transmission interface unit wirelessly communicates with the motion sensing device 20 using a local wireless network (e.g., using Bluetooth or WiFi). In addition, the illustrative motion sensing device 20 is both lightweight (e.g., less than 30 grams) and compact in size (e.g., less than 40 mm by 70 mm by 20 mm) so that it is generally comfortable for the user 14 to wear on his or her head 16.

Next, referring to FIG. 4, an explanation of the three (3) directions of head rotation that the motion sensing device 20 is capable of detecting will be described. First, the motion sensing device 20 is configured to detect the rotation of the head 16 of the user 14 about the yaw axis 22 of rotation as indicated by the curved arrow 24 in FIG. 4. The curved arrow 24 about the yaw axis 22 indicates the common side-to-side movement of the user's head 16 during the vestibular testing and/or training. Secondly, the motion sensing device 20 is configured to detect the rotation of the head 16 of the user 14 about the pitch axis 26 of rotation as indicated by the curved arrow 28 in FIG. 4. The curved arrow 28 about the pitch axis 26 indicates the up-and-down movement of the user's head 16 during the vision testing. Thirdly, the motion sensing device 20 is configured to detect the rotation of the head 16 of the user 14 about the roll axis 30 of rotation as indicated by the curved arrow 32 in FIG. 4. The curved arrow 32 about the roll axis 30 indicates the tilt-right and tilt-left movement of the user's head 16 during the vestibular testing and/or training. In addition to the ability to determine head rotation about all three (3) axes of rotation, the use of a three-dimensional motion sensing device 20 advantageously permits the determination of whether the user 14 is rotating his or her head 16 purely about the desired axis of rotation (e.g., the yaw axis) or whether there is also off-axis rotation of the user's head 16 during the prescribed rotation (e.g., the user 14 is rotating his or head 16 about a combination of the yaw axis and the roll axis, or about a combination of the yaw axis and the pitch axis). Because off-axis rotation may adversely affect the accuracy of the vestibular testing results, it is important to determine if off-axis rotation is present during the vestibular testing of the user 14. The utilization of a three-dimensional motion sensing device 20 enables the determination of this off-axis rotation.

Now, an illustrative manner in which the tablet computing device 102 of the portable vestibular testing and/or training system 100 performs the head rotation calculations from the output of the motion sensing device 20 will be explained in detail. In particular, this calculation procedure will describe the manner in which the angular position and the angular velocity of the head 16 of the user 14 may be determined using the signals from the motion sensing device 20 (i.e., the head-mounted IMU) of the vestibular testing and/or training system 100. As explained above, in one or more embodiments, the motion sensing device 20 may be in the form of an IMU, which includes the following three triaxial sensor devices: (i) a three-axis accelerometer sensing linear acceleration $\vec{a}'$, (ii) a three-axis rate gyroscope sensing angular velocity $\vec{\omega}'$, and (iii) a three-axis magnetometer sensing the magnetic north vector $\vec{n}'$. The motion sensing device 20 (i.e., the IMU) senses in the local (primed) frame of reference attached to the IMU itself. Because each of the sensor devices in the IMU is triaxial, the vectors $\vec{a}'$, $\vec{\omega}'$, $\vec{n}'$ are each 3-component vectors. A prime symbol is used in conjunction with each of these vectors to symbolize that the measurements are taken in accordance with the local reference frame. The unprimed vectors that will be described hereinafter are in the global reference frame.

The objective of these calculations is to find the angular position or orientation $\vec{\theta}(t)$ and the angular velocity $\vec{\omega}(t)$ of the head of the user 14 in the global, unprimed, inertial frame of reference. The initial orientation in the global frame of reference may be either known in advance or derived from $\vec{\theta}_0$, as will be explained below with regard to the rotation transformation matrix.

For the purposes of the calculation procedure, a right-handed coordinate system is assumed for both global and local frames of reference. The global frame of reference is attached to the Earth. The acceleration due to gravity is assumed to be a constant vector $\vec{g}$. Also, for the purposes of the calculations presented herein, it is presumed the sensor devices of the inertial measurement unit (IMU) provide calibrated data. In addition, all of the one or more output signals from the IMU are treated as continuous functions of time. Although, it is to be understood the general form of the equations described herein may be readily discretized to account for IMU sensor devices that take discrete time samples from a bandwidth-limited continuous signal.

The angular velocity $\vec{\omega}(t)$ of the user's head rotation is obtained by coordinate transformation using the IMU output signal(s) as follows:

$$\vec{\omega}(t) = \vec{\Theta}(t)\vec{\omega}'(t) \qquad (1)$$

where $\vec{\Theta}(t)$ is the matrix of the rotation transformation that rotates the instantaneous local frame of reference into the global frame of reference.

The orientation $\vec{\theta}(t)$ of the user's head rotation is obtained by single integration of the angular velocity using the IMU output signal(s) as follows:

$$\vec{\theta}(t) = \vec{\theta}_0 + \int_0^t \vec{\omega}(t)dt \qquad (2)$$

$$\vec{\theta}(t) = \vec{\theta}_0 + \int_0^t \vec{\Theta}(t)\vec{\omega}'(t)dt \qquad (3)$$

There are two aspects to the coordinate transformation matrix $\vec{\Theta}(t)$ calculation: (i) the initial value $\vec{\Theta}_0 \equiv \vec{\Theta}(0)$ at t=0 and (ii) subsequent updates to this value. The updates may be integrated from the angular velocity, i.e., the time derivative $\dot{\Theta}$ of the rotation transformation matrix may be set as a function of the angular velocity, and then the coordinate transformation matrix becomes:

$$\vec{\Theta}(t) = \int_0^t \dot{\Theta}(\tau, \vec{\omega}'(\tau)) d\tau \tag{4}$$

The value at any point in time may be derived from known local and global values of both the magnetic north vector and the acceleration of gravity. Those two vectors are usually non-parallel. This is the requirement for the $\vec{\Theta}(\vec{g}', \vec{n}', \vec{g}, \vec{n})$ to be unique. The knowledge of either of those vectors in isolation gives a family of non-unique solutions $\vec{\Theta}(\vec{g}', \vec{g})$ or $\vec{\Theta}(\vec{n}', \vec{n})$. Both are unconstrained in one component of rotation. The $\vec{\Theta}(\vec{g}', \vec{n}', \vec{g}, \vec{n})$ has many known implementations, with the common one being the Kabsch algorithm.

In one or more embodiments, if a known starting global orientation is assumed, and the time-derivative of the rotation transformation matrix as a function of the angular velocity in the local frame is used, it is possible to obtain the matrix without the need for the accelerometer and magnetometer in the IMU.

Advantageously, in one or more embodiments, the motion sensing device 20 described above requires no manual calibration step or setup time, other than putting the device 20 on the head 16 of the user 14. That is, there is no required manual calibration and/or tare step (e.g., to calibrate the accelerometer with respect to gravity and/or to zero the gyroscope) that must be performed prior to the execution of each particular test or training session. Obviating the need for manual calibration and/or a manual tare step advantageously saves valuable time during the execution of a particular test or training series. In order to avoid these laborious and tedious manual steps, at the beginning of every test or training trial, the motion sensing device 20 (i.e., inertial measurement unit 20) is automatically re-tared (or re-zeroed) to the user's head position at that time by the tablet computing device 102. With each of these zeroing events, the tablet computing device 102 also checks the orientation of the motion sensing device 20 in order to make sure that it is on the user's head 16 correctly and/or to make sure the user 14 is still and has his or her head 16 held in the correct orientation. The tablet computing device 102 checks the orientation of the motion sensing device 20 by using the data from the linear accelerometer, and by determining which axis the gravity vector lies in. If the tablet computing device 102 detects no issues with the orientation of the motion sensing device 20, nothing happens on the user output screen (i.e., no message is displayed in order to save time). Conversely, if the computing device 102 determines that there is a problem with the orientation of the motion sensing device 20, a flag pops up on the user output screen and the test or training session will not begin. In order to begin the test or training session, the user must adjust the motion sensing device 20 on his or her head 16 to the correct position and press "okay" on the tablet computing device 102 to dismiss the flag. Upon the "okay" input, the motion sensing device 20 will tare to its position at that time and the test or training session will begin. In these one or more embodiments, the flag only pops up once per trial.

Also, advantageously, in these one or more embodiments, the motion sensing device 20 does not require a flat and/or still surface for using the motion sensing device 20 (i.e., the inertial measurement unit). In addition, in these one or more embodiments, the motion sensing device 20 does not comprise an electrical cord that operatively connects it to the tablet computing device 102. That is, the motion sensing device 20 is wirelessly coupled to the tablet computing device 102 without the use of any electrical wires. Because the motion sensing device 20 is not tethered (i.e., it contains no electrical cord), it can advantageously accommodate various configurations and distances from the tablet computing device 102. In other words, the configuration of the portable vestibular testing and training system 100 is not limited by the physical limitations imposed upon the system 100 by the fixed length of an electrical cord connecting the motion sensing device 20 to the tablet computing device 102 (e.g., the electrical cord of a tethered motion sensing device 20 may be too short to accommodate a desired testing or training configuration). Also, the portable nature of the computing device 102 advantageously allows the screen to be used at various orientations by the user.

Advantageously, in one or more embodiments, the motion sensing device 20 determines the angular velocity $\vec{\omega}(t)$ of the user's head rotation about a rotational axis extending longitudinally through the user's neck so that the angular velocity may be accurately determined regardless of the position of the user (see e.g., FIGS. 5-7, which illustrate different head positions of the user). When the head of the user is disposed in a typical upright position (e.g., when the user is sitting down in a chair), the angular velocity of the user's head may be determined by processing the angular velocity about the body frame z-axis ($\vec{\omega}_{Bz}$) output by the motion sensing device 20 to determine the head angular velocity about the inertial frame z-axis ($\vec{\omega}_{Iz}$), using the following equation:

$$\vec{\omega}_{Iz} = q^{-1} \vec{\omega}_{Bz} q \tag{5}$$

where:
q: the quaternion at the current timestamp; and
$q^{-1}$: the inverse of the quaternion at the current timestamp.

However, when the user's head is disposed in a position other than an upright vertical position (e.g., when the user is looking down at the tablet computing device 102 or laying down holding the tablet computing device 102, e.g., the positions of FIGS. 6 and 7), the determination of the head angular velocity about the inertial frame z-axis will not accurately determine the desired head angular velocity because the axis about which the head velocity is being determined is no longer vertical in these other body orientations of the user (i.e., leaning over or lying down). As such, to accurately determine the head angular velocity for the user in these other body orientations of the user, the angular velocity of the user's head rotation is determined about a rotational axis extending longitudinally through the user's neck (i.e., $\vec{\omega}_{Nz}$ is determined for the user). In these one or more embodiments, in order to facilitate the determination of the head angular velocity of the user about the neck axis ($\vec{\omega}_{Nz}$), quaternions are used to compute this desired head angular velocity ($\vec{\omega}_{Nz}$).

Firstly, the user is required to sit or stand in a typical upright position in which the neck axis ($v_{N0}$) aligns with the inertial z-axis ($v_I$) as shown in FIG. 5. Then, the quaternion relationship ($q_0$) between the initial body frame axis ($v_{B0}$) and the initial neck axis ($v_{N0}$, also known as $v_I$) is captured, where:

$$v_{I0} = q_0^{-1} v_{B0} q_0 \quad (6)$$

$$v_{I0} = [0,0,0,1] \quad (7)$$

Finally, the head angular velocity of the user about the neck axis ($\vec{\omega}_{Nz}$) is determined using the following equation:

$$\vec{\omega}_{Nz} = q_0^{-1} \vec{\omega}_{Bz} q_0 \quad (8)$$

Advantageously, equation (8) enables the head angular velocity of the user to be accurately determined regardless of the orientation of the user. That is, the head angular velocity of the user may be accurately determined when the user is leaning over, lying down, or in any other position in which the neck axis of the user is not oriented vertically. For example, with reference to FIG. 5, it can be seen that the head 50 of the user is disposed in a generally upright position, but the motion sensing device (e.g., the inertial measurement unit 52) is not oriented perpendicular to the forehead of the user. As such, determining the head angular velocity about the body frame z-axis 54 ($v_B$) would not accurately determine the desired head angular velocity. To accurately determine the head angular velocity, equation (8) above is used to determine the angular velocity of the user's head rotation about a rotational axis 56 ($v_N$) extending longitudinally through the user's neck. As another example, with reference to FIG. 6, it can be seen that the head 50 of the user is disposed in a forward leaning position. As such, similar to the FIG. 5 position, equation (8) is used to accurately determine the angular velocity of the user's head rotation about the neck rotational axis 56 ($v_N$), rather than determining the angular velocity about the body rotational axis 54 ($v_B$). As yet another example, with reference to FIG. 7, it can be seen that the head 50 of the user is disposed in a supine position. As such, similar to the positions in FIGS. 5 and 6, equation (8) is used to accurately determine the angular velocity of the user's head rotation about the neck rotational axis 56 ($v_N$), rather than determining the angular velocity about the body rotational axis 54 ($v_B$).

In one or more alternative embodiments, the angular displacement and velocity of the user's head 16 could be determined using the camera 44 described hereinafter by capturing images of the user's head 16, rather than the motion sensing device 20 described above.

Figure 3:
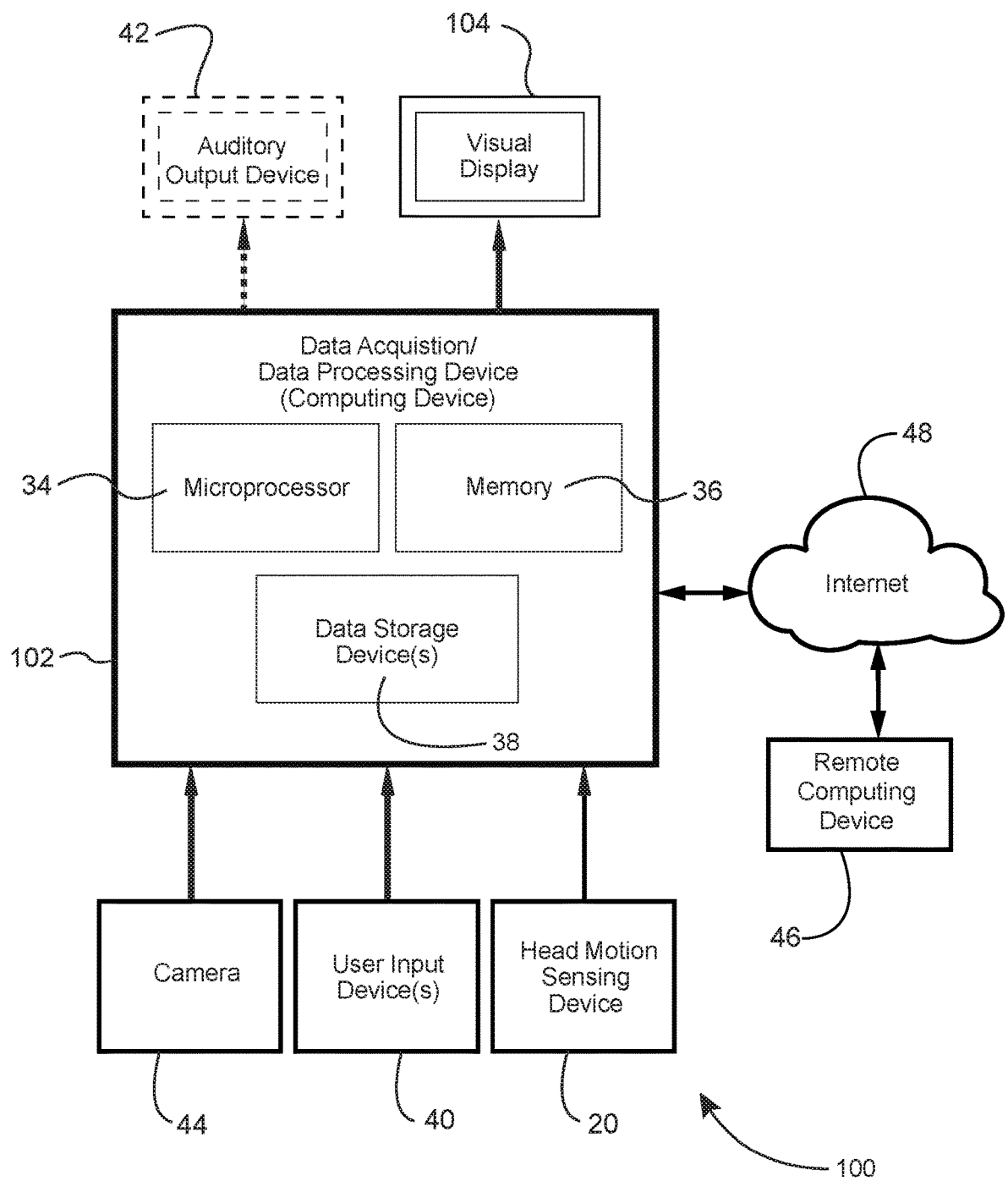
FIG. 3 is a block diagram of constituent components that may be utilized in the embodiments of the vestibular testing and/or training system described herein.

As shown in the illustrative block diagram of FIG. 3, the portable vestibular testing and training system 100 further includes a user input device 40. The user input device 40 is configured to output a signal based upon an input response by the user 14. In the illustrative embodiment, the user input device 40 may comprise the touchscreen user interface of the tablet computing device 102. In other embodiments, the user input device 40 may alternatively comprise (i) a voice recognition device that allows the user 14 to verbally input the user's response (e.g., to record the user's perceived orientation of the optotype), (ii) one or more buttons, (iii) a keyboard (i.e., a virtual or physical keyboard), (iv) a wireless clicking device, and (v) a joystick.

In the illustrative embodiment, during the vestibular testing or training of the user 14, after the user 14 identifies the perceived configuration of the visual object 10 that is displayed on the visual display device 104, the user 14 may use the user input device 40 in order to enter and transmit his or her response (i.e., the perceived configuration of the visual object 10) to the tablet computing device 102. In one or more embodiments, the user input device 40 is configured to accept at least four different responses of the user 14, wherein each of the at least four different responses of the user 14 correspond to different configurations of the visual object 10. For example, referring again to FIG. 2, it can be seen that, if the visual object 10 is in the form of a Tumbling E optotype, a first configuration of the visual object is one in which the Tumbling E is pointing to the right, a second configuration of the visual object is one in which the Tumbling E is pointing to the left, a third configuration of the visual object is one in which the Tumbling E is pointing up, and a fourth configuration of the visual object is one in which the Tumbling E is pointing down. Also, as will be described in more detail hereinafter, the size of the optotype displayed on the visual display device 104 of the tablet computing device 102 may be varied based upon the measured distance of the user 14 to the output screen and/or based upon the difficulty of a particular level. In addition, other configurations of the Tumbling E optotype are possible, such as configurations of the Tumbling E optotype pointing in each of the four forty-five (45) degree angular positions (i.e., pointing up and to the left, pointing up and to the right, pointing down and to the left, and pointing down and to the right).

Now, turning to FIG. 3, it can be seen that the data acquisition/data processing device (i.e., the tablet computing device 102) of the portable vestibular testing and/or training system 100 comprises a microprocessor 34 for processing data, memory 36 (e.g., random access memory or RAM) for storing data during the processing thereof, and data storage device(s) 38, such as one or more internal solid state drives, external flash drives, or any combination thereof. As shown in FIG. 3, the motion sensing device 20 and the visual display device 104 are operatively coupled to the computing device 102 such that data is capable of being transferred between these devices (e.g., the visual display device 104 may be a built-in screen of the tablet computing device 102). Also, as illustrated in FIG. 3, one or more data input devices 40, such as the touchscreen user interface or a voice recognition sensor are operatively coupled to the computing device 102 so that a user is able to enter data into the computing device 102. In one or more alternative embodiments, the computing device 102 may be in the form of a laptop computing device or a desktop computer, rather than the tablet computing device of the illustrative embodiment.

Referring again to FIG. 3, it can be seen that an auditory output device 42 may also be operatively coupled to the computing device 102 of the vestibular testing and/or training system 100. The auditory output device 42 may comprise one or more speakers or an audio headset that is configured to be worn by the user 14. During the vestibular testing or training sessions wherein the user displaces his or her head 16, the computing device 102 may be specially programmed to generate and output a first audible indicator (e.g., a series of beeps) via the auditory output device 42 that indicates whether or not the velocity or speed (e.g., the peak angular velocity) at which the user 14 is displacing his or her head lies within a predetermined range. In addition, the auditory output device 42 also may provide sound for a movie that the user 14 is watching while he or she performs the vestibular test or training session.

As an alternative to, or in addition to, generating instructional cues for the user 14 using the auditory output device 42, the computing device 102 may be specially programmed to generate and display a first visual indicator (e.g., a change in the color of a selected area) on the output screen of the visual display device 104 that indicates whether or not the velocity or speed at which the user 14 is displacing his or her head lies within the predetermined range. Also, as an alternative to, or in addition to, generating instructional cues for the user 14 using the auditory output device 42, the computing device 102 may be specially programmed to generate and display a second visual indicator (e.g., a displaceable dot indicator) on the output screen of the visual display device that indicates whether or not the user 14 is displacing his or her head over a prescribed range of motion.

In one or more embodiments, the user input device 40, the visual display device 104, and the data processing device 102 are constituent components of a handheld tablet computing device or a laptop computing device.

Turning again to FIG. 3, it can be seen that a camera 44 may also be operatively coupled to the computing device 102 of the vestibular testing and/or training system 100. In the illustrative embodiment, the camera 44 may capture a plurality of eye images of the user 14 while the user is being tested using the system, and the computing device 102 may be configured to determine the eye movement of the user 14 based upon the plurality of eye images of the user 14 captured by the camera 44. Advantageously, the determination of the eye movement of the user 14 allows a clinician to determine how the eyes of the user 14 move relative to the head 16 for assessing vestibular function. The determination of the eye movement of the user 14 allows the clinician to determine eye performance parameters, such as retinal slip.

In one or more embodiments, the camera 44 is disposed on or in the front surface of the tablet computing device or the laptop computing device (e.g., see FIGS. 1 and 2).

In addition, as shown in FIG. 3, the vestibular testing and/or training system 100 further comprises a data interface operatively coupling the computing device 102 of the portable system to a remote electronic device (e.g., remote computing device 46) via a network (e.g., via the Internet 48) so that data from the computing device 102 is capable of being transmitted to the remote electronic device 46. In one or more embodiments, the data interface may comprise a wireless data interface or a wired data interface operatively coupling the computing device 102 to the Internet 48.

In one or more embodiments, the information transferred between the computing device 102 of the portable system and the remote computing device 46 is encrypted so that both the privacy of the user 14, as well as sensitive information about him or her (e.g., his or her location) is protected. For example, a Health Insurance Portability and Accountability Act (HIPAA) compliant link may be established between the computing device 102 of the portable system and the remote computing device 46 during the remote monitoring of the user's progress.

In one or more embodiments, the first visual indicator may comprise a sliding bar visual indicator in order to indicate whether or not the velocity or speed at which the user 14 is displacing his or her head lies within the predetermined range. In these one or more embodiments, the displacement of the sliding bar visual indicator is controlled by the velocity or speed of the user's head 16. That is, if the user 14 is displacing his or her head 16 at a slow speed, the sliding bar visual indicator will only travel a small distance. In contrast, if the user 14 is displacing his or her head 16 at a high speed, the sliding bar visual indicator will travel a large distance. Also, because the sliding bar visual indicator may also indicate the direction of travel of the user's head 16 (i.e., the sliding bar visual indicator is displaced to the left when the user's head 16 is displaced to the left and the sliding bar visual indicator is displaced to the right when the user's head 16 is displaced to the right). In addition, if the user 14 displaces his or her head 16 at a velocity that is higher than the predetermined range, the sliding bar visual indicator may be changed from a first color to a second color to indicate a saturation of the head velocity or speed.

In one or more embodiments, the portable vestibular testing and/or training system 100 may further comprise means for determining a distance and/or tilt of the head 16 of the user 14 relative to the visual display device 104. In some embodiments, the means for determining a distance and/or tilt of the head of the 14 user may comprise the camera 44 that is configured to capture one or more images of a visual feature on the head 16 of the user 14 (e.g., a dot on the head 16 of the user 14). In these embodiments, the computing device 102 is configured to determine the distance between the head 16 of the user 14 and the visual display device 104 based upon a size of the visual feature (e.g., the dot or optical E) in the one or more images captured by the camera 44. The distance measurement may be used by the computing device 102 to change the size of the optotype or other identifiable visual object that is displayed to the user 14 based upon an assessment of the baseline visual acuity of the user 14. In addition, the computing device 102 may be programmed to automatically change the size of the optotype or other identifiable visual object based upon the measured distance between the head 16 of the user 14 and the visual display device 104 (e.g., if the user 14 is further away from the display, the optotype is larger; conversely, if the user 14 is closer to the display, the optotype is smaller). Also, in these embodiments, the computing device 102 may be configured to further determine the tilt of the head 16 of the user 14 relative to the visual display device 104 based upon a size comparison of two or more adjacent visual features (e.g., a size comparison of two adjacent dots on the head 16 of the user 14) in the one or more images captured by the camera 44, or based upon a distortion of the visual feature (e.g., a distortion of a dot) in the one or more images captured by the camera 44. The tilt of the head 16 of the user 14 determined by the computing device 102 may be used to determine if the user 14 is looking at the visual display device 104 properly (i.e., if the user 14 is looking straight at the screen, rather than at an angle, etc.) because this could affect the results of the vestibular testing and/or training (e.g., if the user 14 is not looking straight at the screen, he or she may be less likely to properly identify the configuration of the visual object 10).

For example, the distance between the head 16 of the user 14 and the visual display device 104 may be computed using the following equation:

$$d = \frac{C}{r} \tag{9}$$

where:
d: distance between the visual feature on the head 16 of the user 14 and the visual display device 104;
C: a constant; and
r: radius or other size parameter of the visual feature (e.g., dot).

The tilt of the head 16 of the user 14 relative to the visual display device 104 may be computed using the following equations:

$$\cos a_0 = \frac{d_1^2 + d_2^2 - d_0^2}{2 \cdot d_1 \cdot d_2} \quad (10)$$

$$\cos a_2 = \frac{d_1^2 + d_0^2 - d_2^2}{2 \cdot d_1 \cdot d_0} \quad (11)$$

$$\alpha = a_2 - \frac{(180 - a_0)}{2} \quad (12)$$

where:
  $d_1, d_2$: distances between the adjacent visual features the head 16 of the user 14 and the visual display device 104; and
  $\alpha$: tilt of the head 16 of the user 14.

In one or more alternative embodiments, the means for determining a distance and/or tilt of the head 16 of the user 14 comprises a distance detection device (e.g., an ultrasonic sensor or infrared sensor) with a transmitter portion for emitting an ultrasonic or infrared pulse and a receiver portion for receiving the ultrasonic or infrared pulse after it is reflected off the head 16 of the user 14. Also, the motion sensing device 20 described above could also be used as the means for determining the distance of the head 16 of the user 14 from the visual display device 104.

In one or more embodiments, the portable vestibular testing and/or training system 100 may further determine the orientation of the computing device 102 (e.g., when the computing device 102 is in the form of a handheld tablet computing device) relative to the user 14 by using the one or more internal inertial measurement units (IMUs) of the tablet computing device. Advantageously, determining the orientation of the tablet computing device allows the user 14 to hold the tablet in any orientation that is convenient for him or her without compromising the accuracy of the testing and/or training protocol by adjusting the screen image accordingly (e.g., by rotating the screen image automatically when the user rotates the tablet computing device). The determination of the orientation of the tablet may also be used by the remote user (e.g., therapist or clinician) to restrict the orientation of the tablet for specific exercises.

2. Vestibular Testing and Training Procedures

In the illustrative embodiment, while the user 14 displaces his or her head 16 at a velocity or speed within a predetermined range (e.g., between 85 and 120 degrees per second) as measured by the motion sensing device 20, one or more configurations of the optotype 10 having a predetermined size are displayed on the output screen of the visual display device 104. For example, different configurations of the Tumbling E optotype may be displayed one-at-time on the output screen of the visual display device 104. In the illustrative embodiment, the optotypes may be superimposed on the scenes of a movie that the user 14 is watching on the visual display device 104 so as to engage the user 14 in the visual task, and keep the user engaged in the visual task. In the illustrative embodiment, the displacement of the user's head 16 may comprise rotating the user's head 16 to the right, and to the left, about the yaw axis 22 of FIG. 4 (i.e., approximately in a horizontal plane). In one embodiment, the optotype 10 is only displayed on the output screen of the visual display device 104 when the head 16 of the user 14 is being rotated within the predetermined angular velocity range (e.g., between 85 and 120 degrees per second) for a requisite number of head sweeps. In one or more embodiments, the Tumbling E optotype is displayed after the user 14 gets the three (3) required head sweeps in a predetermined target velocity range (e.g., 85 deg./sec. to 120 deg./sec.). Also, in or more embodiments, the velocity profile of the head movement also may be considered in evaluating the performance of the user 14. During the vestibular testing or training procedure, the computing device 102 may be specially programmed to randomly choose the orientation of the optotype that is displayed on the screen. Also, during the vestibular testing or training procedure, the computing device 102 may be specially programmed to randomly choose whether to display the optotype on a left head turn or a right head turn. In addition, the first visual indicators described above may be used to ensure that the user's head 16 is rotated within the predetermined velocity range, while the second visual indicator may be used to ensure that the user's head 16 is rotated within the prescribed range of motion (e.g., between 20 degrees to the left and 20 degrees to the right, or between 30 degrees to the left and 30 degrees to the right).

In the illustrative embodiment, after the optotype disappears during the vestibular testing or training procedure, the user 14 continues to shake his or her head, but enters an orientation response into the user input device 40 identifying the orientation of the optotype 10 that appeared on the screen. During the testing or training procedure, the user 14 is also permitted to stop rotating his or her head 16, which results in the testing or training procedure entering into a "pause" state. If the "pause" state is initiated, the computing device 102 is specially programmed to indicate a detected zero (0) head velocity at the bottom of the screen, and to further generate instructions on the screen that instruct the user 14 to resume rotating his or her head when ready. In one or more embodiments, approximately five-hundred (500) milliseconds after the user 14 records the orientation response, the next trial of the vestibular test or training procedure begins, wherein another optotype is displayed after the user 14 gets the three (3) required head sweeps in the predetermined target velocity range. If a trial of the vestibular test or training procedure lasts for more than eight (8) seconds, the computing device 102 may be specially programmed to interrupt the trial, and to mark the trial as "unable to complete".

Figure 4:
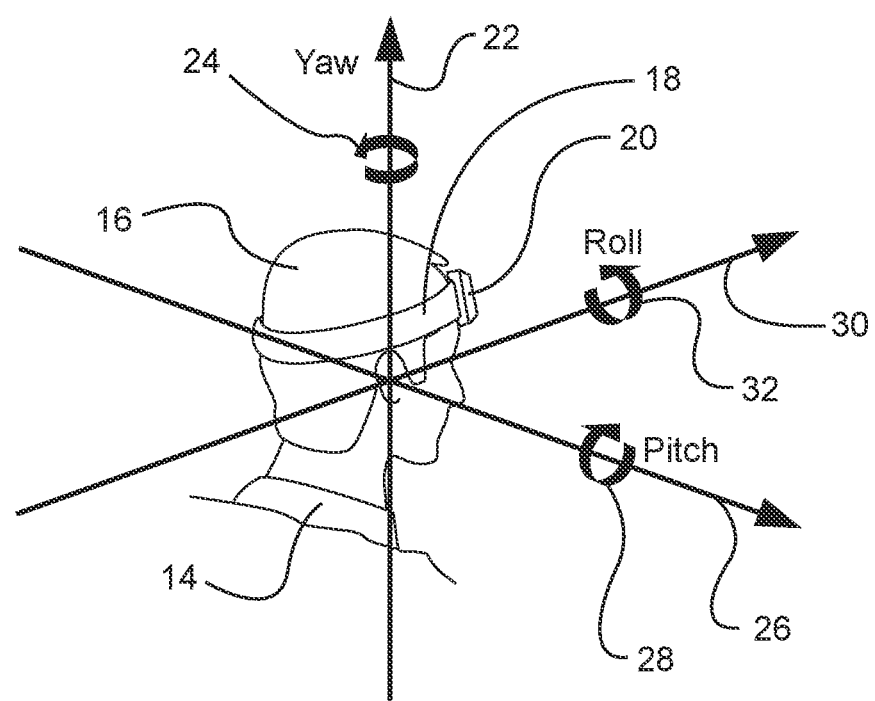
FIG. 4 is a diagrammatic view of the directions of user head rotation that are capable of being measured with the motion sensing device of the portable vestibular testing and/or training system described herein.

In alternative embodiments, rather than rotating his or her head 16 about the yaw axis 22 in FIG. 4, the user 14 may alternatively rotate his or her head 16 about the pitch axis 26 (i.e., approximately in a vertical plane) or about the roll axis 30 (i.e., in a roll plane). In these alternative embodiments, the computing device 102 is specially programmed to allow the user 14 to selectively choose any one of these rotational directions when performing the vestibular test or training procedure. In one embodiment, when the rotation about the pitch axis 26 is selected the optotype 10 is only displayed on the output screen of the visual display device 104 when the head 16 of the user 14 is being rotated within a predetermined angular velocity range (e.g., between 60 and 85 degrees per second).

In the illustrative embodiment, during the vestibular test or training procedure, the head velocity of the user 14, as measured by the motion sensing device 20, is used by the computing device 102 in order to determine when to display the optotype so that the optotype will generally be shown at a position centered around the user's zero position. The user's zero position is set at the beginning of each trial when the user 14 is generally still and looking straight ahead at the visual display device 104. During the sweep in which the optotype (e.g., Tumbling E optotype) will be shown, an optimal trigger angle is calculated by the computing device 102 at each sample based on the instantaneous angular velocity of the user's head 16 and the length of time for which the optotype must be displayed. When the most recent angle calculated is reached, the optotype begins to show on the screen of the visual display device 104. The optimal trigger angle may be calculated by the computing device 102 as follows:

$$\theta_T = \frac{\dot{\theta}[(t)(10^{-3})]}{2} \quad (13)$$

where:
$\dot{\theta}$: instantaneous head velocity in the IMU plane of testing in degrees per second; and
t: length of time in milliseconds (ms) that the optotype will be displayed on the screen.

In the illustrative embodiment, the calculation described in equation (13) is iterated with each sample until the trigger angle $\theta_T$ is reached, in which case, the optotype is triggered to display. Because the user's zero position is set when the user 14 is generally still and looking straight ahead at the visual display device 104, the trigger angle $\theta_T$ calculated in equation (13) is divided by two (2).

In one or more embodiments, during the performance of the vestibular test or training procedure, the computing device 102 may be specially programmed to generate an audio output signal that corresponds to the proper head sweeping of the user 14, and to output that audio output signal to external or internal speakers of the computing device 102 in order to assist the user 14 with the proper head sweep timing that is required for the vestibular tests or training sessions (i.e., a metronome plays from the speakers to assist the user 14 with the execution of the head sweep timing). The metronome may provide an audible indicator of the pace at which the user's head should be rotated during the vestibular tests or training sessions. As such, the metronome may supplement the visual indicator(s) that is provided on the screen of the visual display device 104. The exact timing of the metronome will vary based upon the particular user being tested.

During each trial of the vestibular test or training procedure, the computing device 102 determines whether or not the user 14 correctly identifies one or more configurations of the visual object 10. For example, the user 14 may be presented with one or more optotypes having a particular configuration (e.g. a Tumbling E pointing to the right—see FIG. 2). After the optotype is displayed to the user 14, the user 14 may utilize the user input device 40 (e.g., a touchscreen user interface or voice recognition device) in order to transmit the response to the computing device 102. After receiving each of the user's responses, the computing device 102 is specially programmed to determine if the user 14 correctly determined the configuration of the optotype that was displayed on the output screen of the visual display device 104. For example, if the Tumbling E optotype 10 of FIG. 2 was displayed on the screen, the user 14 must indicate that optotype is pointing to the right to get the identification correct. Any other answer would be incorrect for this configuration of the optotype. Once the user's answer or response is evaluated as to its correctness, the computing device 102 is specially programmed to record whether or not the user 14 identified the optotype correctly. In the illustrative embodiment, after the computing device 102 records the user's answer or response, an optotype having a different configuration is presented to the user 14.

In this manner, the computing device 102 is specially programmed to display a series of different visual objects (i.e., the optotypes) on the output screen of the visual display device 104 during a set of successive trials while the user 14 displaces his or her head at a velocity or speed within the predetermined range as measured by the motion sensing device 20 (e.g., during ten (10) or more trials). In the illustrative embodiment, after each optotype is displayed on the output screen of the visual display device 104, the computing device 102 is specifically programmed to determine whether or not the user 14 correctly identified the configuration of the optotype.

In the illustrative embodiment, after the user 14 has completed a predetermined number of trials of optotype identification, the computing device 102 may be specifically programmed to determine an overall score for the exercise. For example, after the user 14 completes a series of ten (10) trials of optotype identification, the computing device 102 determines the score for that particular exercise.

In one or more embodiments, the computing device 102 is further programmed to generate one or more interactive exercises for the user 14 containing the one or more visual objects on the output screen of the visual display device 104, the one or more interactive exercises including one or more parameters affecting the difficulty of the one or more interactive exercises for the user 14; and the remote electronic device 46 is programmed so as to allow a remote user to modify the one or more parameters affecting the difficulty of the one or more interactive exercises for the user 14. That is, the remote user (e.g., a therapist or clinician) is able to remotely change the one or more parameters based on the performance of the user (e.g., patient). For example, the remote user may receive a notification when the user has completed his or her training, and then can make it easier or more difficult for the user based on the previous performance of user. The one or more visual objects displayed on the output screen of the visual display device 104 may comprise one or more identifiable visual objects (e.g., different types of cars, trucks, or airplanes) superimposed on one or more scenes of a movie. Advantageously, superimposing the identifiable visual objects on a dynamic background in the form of a movie makes the testing far more engaging and entertaining for the user 14 because the user 14 is able to watch a movie of his or her choice while performing the testing. In these one or more embodiments, the one or more identifiable visual objects may be identified by the user by using the user input device 40, and the one or more parameters affecting the difficulty of the one or more interactive exercises for the user 14 may comprise a location of the one or more identifiable visual objects on the output screen of the visual display device 104 (e.g., center or periphery of the screen). Also, in these one or more embodiments, the computing device 102 may be further programmed to determine which ones of the one or more identifiable visual objects (e.g., cars, trucks, or airplanes) are displayed on the output screen of the visual display device 104 based upon a particular theme selected by the user 14 using the user input device 40 (e.g., if the user 14 selects a theme relating to aviation, then different types of airplanes may be displayed on the screen). For example, the computing device 102 may be programmed to automatically select the type of identifiable visual objects that are displayed on the output screen of the visual display device 104 based on the theme of the movie selected by the user 14 (e.g., if the user 14 is watching a movie containing airplanes, then airplanes are displayed on the visual display device 104 by the computing device 102). To make the testing or training more difficult, the remote user via the remote computing device 46 is able to specify that the one or more identifiable visual objects appear in the center of the screen or at various locations on the screen. This adds another level of testing or training mode complexity.

In addition to, or as an alternative to, superimposing the one or more identifiable visual objects (e.g., different types of cars, trucks, or airplanes) on the one or more scenes of a movie, the computing device 102 may be programmed to generate a plurality of different visual backgrounds of varying complexity, and to display a particular one of the plurality of different visual backgrounds on the output screen of the visual display device 104 together with the one or more identifiable visual objects. The computing device 102 may be further programmed to select the particular one of the plurality of different visual backgrounds that is displayed on the output screen of the visual display device 104 based upon a difficulty level of a visual exercise being performed by the user 14. Background settings may be changed to make the testing or training more difficult. It is more difficult to determine the orientation of the optotype (or similar protocol) when the contrast of the background varies. The initial setting could be a monotone background, and then increase in complexity. For example, a static background with varying contrasts or a picture could be the next level. A third level could include a static background that "moves" in various directions or optokinetic flow. Finally, a video background could be used for the highest level of difficulty.

In one or more embodiments, the computing device 102 is further programmed to generate a game-type user interface with the one or more identifiable visual objects (e.g., different types of cars, trucks, or airplanes) disposed on the particular one of the plurality of different visual backgrounds and a score indicating a quantity of the one or more visual objects identified correctly by the user. The game-type user interface generated by the computing device 102 may further include a game performance summary indicating a total quantity of the one or more visual objects that the user has attempted to identify, and the difficulty level of the visual exercise, in the addition to the score. For example, in a training mode, the computing device 102 may be programmed to tabulate how many correct identifiable visual objects were completed in the amount of time allotted and formulate a score based on the overall performance with other factors taken into consideration, such as time allotted and ratio of correct/incorrect objects, and the difficulty of the training mode settings. A user symptom score may also be entered before and after exercise to track the symptoms of the user 14. The computing device 102 also may be programmed to compare the user's score to previous users, and display the comparison to the user 14 so as to provide motivation for improving speed and accuracy. Performance may be tracked over time and the game parameters may be adjusted as the user 14 improves so as to keep the training challenging. The user 14 is given a score at the end of the training to make it competitive and game-like to engage the user and improve compliance.

Also, in one or more embodiments, the one or more interactive exercises generated by the computing device 102 may comprise a plurality of different levels, and the computing device 102 may be further programmed to advance to a successive one of the plurality of different levels when the user 14 performs a particular one of the one or more interactive exercises correctly so as to increase the difficulty of the one or more interactive exercises. In these one or more embodiments, the computing device 102 may be further programmed to adjust the location of the one or more identifiable visual objects (e.g., different types of cars, trucks, or airplanes) on the output screen of the visual display device 104 from a central location on the output screen to a peripheral location on the output screen as the difficulty of the one or more interactive exercises is increased. The computing device 102 may be programmed to automatically make the testing or training modes more challenging if the performance score of the user 14 is above a certain threshold.

In addition, in one or more embodiments, the remote electronic device 46 is further programmed so as to allow a remote user to advance the user 14 to the successive one of the plurality of different levels via the network (e.g., via the Internet 48).

In one or more further embodiments, the computing device 102 is further programmed to generate one or more reports indicative of the performance of the user 14 during the one or more interactive exercises, and to transmit the one or more reports to the remote electronic device 46 so that the remote user is able to remotely track the progress of the user 14 during the one or more interactive exercises and modify the one or more parameters if deemed necessary. Alternatively, rather than the portable computing device 102 generating the reports, the remote electronic device 46 may be programmed to generate the one or more reports indicative of the performance of the user 14 during the one or more interactive exercises so that the remote user is able to remotely track the progress of the user 14 during the one or more interactive exercises and modify the one or more parameters if deemed necessary. The reports generated and sent to the remote user may indicate the time that the user (e.g., patient) spent doing the exercises and success rates so that the remote user (e.g., clinician) may keep track of the user's progress and adjust the parameters as necessary. For example, the user may be instructed to complete a certain amount of training, as determined by the remote clinician. After the training, a report may be sent back to the clinician for review. The clinician can then set the parameters for future training based on the performance in the reports. The remote user, by means of the remote computing device 46, is able to receive and print out the reports of the training and track the progress of the user 14 over time so as to adjust the settings so that the training is at a level that challenges the user 14.

In yet one or more further embodiments, the computing device 102 is further programmed to generate a data file that tracks time and date, input settings, head movement over time, and outcomes of the testing and/or training for the user 14.

In still one or more further embodiments, the computing device 102 is configured to transmit one or more images of the user 14 captured by the camera 44 to the remote electronic device 46 so that the remote user is able to remotely direct the user on the proper technique for performing the one or more interactive exercises. That is, the video of the user 14 performing the exercises may be sent to the remote electronic device 46 so that the remote user may provide "coaching" to make sure the user 14 is performing the exercises correctly since they will not be in the room to instruct the user 14. Notes could be generated and remotely sent back to the user 14 before the next training session.

In yet one or more further embodiments, the computing device 102 and/or the remote computing device 46 is further programmed to generate a record of the settings used for the exercise and scorekeeping data after each use which can be shared with the remote user (e.g., clinician) to function as part of clinical oversight and quality.

While reference is made throughout this disclosure to, for example, "an illustrative embodiment", "one embodiment", or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A portable system for vestibular testing and/or training of a user, said system comprising:
    a user input device, the user input device configured to output a signal based upon an input response by the user;
    a motion sensing device, the motion sensing device configured to measure a velocity or speed of a head of the user;
    a visual display device having an output screen, the visual display device configured to display one or more visual objects on the output screen so that the one or more visual objects are visible to the user; and
    a data processing device, the data processing device operatively coupled to the user input device, the motion sensing device, and the visual display device, the data processing device being programmed to:
        determine one or more visual objects out of a plurality of visual objects that are to be displayed on the output screen of the visual display device based upon a particular theme selected by the user using the user input device;
        display the one or more visual objects on the output screen of the visual display device based upon whether the user's head undergoes displacement at a velocity or speed within a predetermined range as measured by the motion sensing device, the one or more visual objects being superimposed on a dynamic background displayed on the output screen of the visual display device; and
        determine whether or not the user correctly identifies the one or more visual objects based upon the signal from the user input device.

2. The portable system according to claim 1, wherein the motion sensing device comprises an inertial measurement unit that includes at least one of an accelerometer, a gyroscope, and a magnetometer; and wherein the data processing device is operatively coupled to the inertial measurement unit by means of a wireless connection.

3. The portable system according to claim 1, wherein the user input device comprises at least one of: (i) a touchscreen user interface, (ii) a voice recognition device, (iii) one or more buttons, (iv) a keyboard, (v) a clicking device, and (vi) a joystick; and
    wherein the user input device is configured to accept a plurality of different responses from the user, each of the plurality of different responses of the user corresponding to a different visual object.

4. The portable system according to claim 1, wherein the one or more visual objects displayed on the output screen of the visual display device comprise one or more optotypes, the one or more optotypes comprising at least one of: (i) a Tumbling E, (ii) a Landolt C, (iii) different letters of a recognized alphabet, and (iv) any other identifiable symbol.

5. The portable system according to claim 1, wherein the user input device, the visual display device, and the data processing device are constituent components of a handheld tablet computing device or a laptop computing device.

6. The portable system according to claim 1, further comprising a camera configured to capture a plurality of eye images of the user while the user is being tested using the system; and
    wherein the data processing device is further operatively coupled to the camera, the data processing device being configured to determine the eye movement of the user based upon the plurality of eye images of the user captured by the camera.

7. The portable system according to claim 1, further comprising an eye movement tracking device configured to track eye movement and/or eye position of the user, the eye movement tracking device comprising at least one of the following: (i) a video camera, (ii) an infrared sensor, (iii) an ultrasonic sensor, and (iv) an electrooculographic sensor;
    wherein the data processing device is further operatively coupled to the video camera, the infrared sensor, the ultrasonic sensor, and/or the electrooculographic sensor, the data processing device being configured to determine the eye movement and/or eye position of the user based upon output from the video camera, the infrared sensor, the ultrasonic sensor, and/or the electrooculographic sensor.

8. The portable system according to claim 1, further comprising means for determining a distance and/or tilt of the head of the user relative to the visual display device; and
    wherein the means for determining a distance and/or tilt of the head of the user comprises a camera configured to capture one or more images of a visual feature on the head of the user, or a distance detection device with a transmitter portion for emitting an ultrasonic or infrared pulse and a receiver portion for receiving the ultrasonic or infrared pulse after it is reflected off the head of the user.

9. The portable system according to claim 8, wherein the means for determining a distance and/or tilt of the head of the user comprises a camera configured to capture one or more images of a visual feature on the head of the user; and
    wherein the data processing device is further operatively coupled to the camera, the data processing device being configured to determine the distance between the head of the user and the visual display device based upon a size of the visual feature in the one or more images captured by the camera, and wherein the data processing device is further configured to determine the tilt of the head of the user relative to the visual display device based upon a size comparison of two or more adjacent visual features in the one or more images captured by the camera, or based upon a distortion of the visual feature in the one or more images captured by the camera.

10. The portable system according to claim 1, further comprising a data interface operatively coupling the data processing device of the portable system to a remote electronic device via a network so that data from the data processing device is capable of being transmitted to the remote electronic device; and wherein the data interface comprises a wireless data interface or a wired data interface operatively coupled to the data processing device, and wherein the network coupling the data processing device of the portable system to the remote electronic device comprises an internet-based network.

11. The portable system according to claim 10, wherein the data processing device is further programmed to generate one or more interactive exercises for the user containing the one or more visual objects on the output screen of the visual display device, the one or more interactive exercises including one or more parameters affecting the difficulty of the one or more interactive exercises for the user; and wherein the remote electronic device is programmed so as to allow a remote user to modify the one or more parameters affecting the difficulty of the one or more interactive exercises for the user.

12. The portable system according to claim 11, wherein the dynamic background on which the one or more visual objects are superimposed comprises one or more scenes of a movie; and wherein the one or more parameters affecting the difficulty of the one or more interactive exercises for the user comprise a location of the one or more visual objects on the output screen of the visual display device.

13. The portable system according to claim 12, wherein the one or more interactive exercises generated by the data processing device comprise a plurality of different levels;

wherein the data processing device is further programmed to advance to a successive one of the plurality of different levels when the user performs a particular one of the one or more interactive exercises correctly so as to increase the difficulty of the one or more interactive exercises;

wherein the data processing device is additionally programmed to adjust the location of the one or more visual objects on the output screen of the visual display device from a central location on the output screen to a peripheral location on the output screen as the difficulty of the one or more interactive exercises is increased; and wherein the remote electronic device is further programmed so as to allow the remote user to advance the user to the successive one of the plurality of different levels via the network.

14. The portable system according to claim 10, wherein the remote electronic device is further programmed to generate one or more reports indicative of the performance of the user during the one or more interactive exercises so that the remote user is able to remotely track the progress of the user during the one or more interactive exercises and modify the one or more parameters if deemed necessary.

15. The portable system according to claim 10, further comprising a camera configured to capture one or more images of the user while the user is being tested using the system; and wherein the data processing device is further operatively coupled to the camera, the data processing device being configured to transmit the one or more images of the user captured by the camera to the remote electronic device so that the remote user is able to remotely direct the user on the proper technique for performing the one or more interactive exercises.

16. The portable system according to claim 1, wherein the data processing device is further programmed to generate a plurality of different dynamic backgrounds of varying complexity, and to display a particular one of the plurality of different dynamic backgrounds on the output screen of the visual display device together with the one or more visual objects, and wherein the data processing device is additionally programmed to select the particular one of the plurality of different visual backgrounds that is displayed on the output screen of the visual display device based upon a difficulty level of a visual exercise being performed by the user.

17. The portable system according to claim 16, wherein the data processing device is further programmed to generate a game-type user interface with the one or more visual objects disposed on the particular one of the plurality of different dynamic backgrounds and a score indicating a quantity of the one or more visual objects identified correctly by the user; and wherein the game-type user interface generated by the data processing device further includes a game performance summary indicating a total quantity of the one or more visual objects that the user has attempted to identify, and the difficulty level of the visual exercise, in the addition to the score.

18. The portable system according to claim 1, wherein the dynamic background on which the one or more visual objects are superimposed comprises one or more scenes of a movie.

19. The portable system according to claim 1, wherein the data processing device is programmed to determine an angular velocity of the head of the user about an inertial frame neck axis of the user using output data from the motion sensing device so that the angular velocity of the head of the user is capable of being accurately determined regardless of the orientation of the user.

20. The portable system according to claim 19, wherein the data processing device is further programmed to determine the angular velocity of the head of the user about the inertial frame neck axis of the user by using quaternion angles to transform the angular velocity of the head of the user about a body frame axis determined using output data from the motion sensing device to the angular velocity of the head of the user about the inertial frame neck axis of the user.

21. A portable system for vestibular testing and/or training of a user, said system comprising:

a user input device, the user input device configured to output a signal based upon an input response by the user;

a motion sensing device, the motion sensing device configured to measure a velocity or speed of a head of the user;

a visual display device having an output screen, the visual display device configured to display one or more visual objects on the output screen so that the one or more visual objects are visible to the user;

a distance measuring device for determining a distance of the head of the user relative to the visual display device; and a data processing device, the data processing device operatively coupled to the user input device, the motion sensing device, the visual display device, and the distance measuring device, the data processing device being programmed to:

determine a dynamic background that is to be displayed on the output screen of the visual display device based upon a particular theme selected by the user using the user input device;

determine one or more visual objects out of a plurality of visual objects that are to be displayed on the output screen of the visual display device based upon the dynamic background that is to be displayed on the output screen;

determine a display size of the one or more visual objects based upon the distance of the head of the user relative to the visual display device determined using the distance measuring device;

display the one or more visual objects having the display size on the output screen of the visual display device while the user's head undergoes displacement at a velocity or speed within a predetermined range as measured by the motion sensing device, the one or more visual objects being superimposed on the dynamic background displayed on the output screen of the visual display device; and determine whether or not the user correctly identifies the one or more visual objects based upon the signal from the user input device.

* * * * *